United States Patent
Arai et al.

(10) Patent No.: US 9,649,103 B2
(45) Date of Patent: May 16, 2017

(54) KNOTLESS ANCHOR

(71) Applicant: Smith & Nephew, Inc., Memphis, TN (US)

(72) Inventors: Tatsuya Arai, Houston, TX (US); Matthew E. Koski, Westford, MA (US)

(73) Assignee: Smith & Nephew, Inc., Memphis, TN (US)

(*) Notice: Subject to any disclaimer, the term of this patent is extended or adjusted under 35 U.S.C. 154(b) by 204 days.

(21) Appl. No.: 14/435,036

(22) PCT Filed: Oct. 31, 2013

(86) PCT No.: PCT/US2013/067858
§ 371 (c)(1),
(2) Date: Apr. 10, 2015

(87) PCT Pub. No.: WO2014/071066
PCT Pub. Date: May 8, 2014

(65) Prior Publication Data
US 2015/0282801 A1   Oct. 8, 2015

Related U.S. Application Data

(60) Provisional application No. 61/721,614, filed on Nov. 2, 2012.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 17/0485* (2013.01);
(Continued)

(58) Field of Classification Search
CPC ............ A61B 17/0401; A61B 17/0485; A61B 2017/0409; A61B 2017/0412;
(Continued)

(56) References Cited

U.S. PATENT DOCUMENTS 5,505,735 A * 4/1996 Li .................. A61F 2/0811
606/232
5,662,654 A  9/1997 Thompson
(Continued)

FOREIGN PATENT DOCUMENTS

| EP | 1199035 A1 | 4/2002 |
| WO | 9516398 A1 | 6/1995 |
| WO | 9516399 A1 | 6/1995 |

OTHER PUBLICATIONS

International Search Report and Written Opinion for PCT/US2013/067858 mailed Feb. 18, 2014.
(Continued)

*Primary Examiner* — Robert Lynch
(74) *Attorney, Agent, or Firm* — Burns & Levinson LLP; Joseph M. Maraia

(57) ABSTRACT

A knotless anchor (100) includes an elongate body (102), a plurality of wings (104) extending outward from the body, a plurality of grooves (106) corresponding to the wings formed in the body, and a transverse bore (110) in communication with the grooves. The wings may be pivotably attached to the body, allowing movement between an open position, where the wings do not engage the grooves, and a closed position, where at least a portion of each wing engages its corresponding groove. A suture (122) routed through the grooves and the transverse bore is frictionally secured to the suture when the wings are urged in the closed position. In use, the wings may be urged into the closed position when inserted into a recess smaller than the cross-section of the anchor, such as a hole formed in a bone.

4 Claims, 13 Drawing Sheets

(52) U.S. Cl.
CPC ............... *A61B 2017/0403* (2013.01); *A61B 2017/0409* (2013.01); *A61B 2017/0412* (2013.01); *A61B 2017/0414* (2013.01); *A61B 2017/0427* (2013.01); *A61B 2017/0437* (2013.01); *A61B 2017/0443* (2013.01); *A61B 2017/0454* (2013.01); *A61B 2017/0456* (2013.01); *A61F 2002/0817* (2013.01); *A61F 2002/0823* (2013.01); *A61F 2002/0835* (2013.01)

(58) Field of Classification Search
CPC .... A61B 2017/0414; A61B 2017/0427; A61B 2017/0456; A61F 2/0811; A61F 2002/0817; A61F 2002/0823; A61F 2002/0835; A61F 2002/0841; A61F 2002/0847; A61F 2002/0852
See application file for complete search history.

(56) References Cited

U.S. PATENT DOCUMENTS

| | | |
|---|---|---|
| 7,780,701 B1 | 8/2010 | Meridew et al. |
| 8,486,120 B2 * | 7/2013 | Shimko ............... A61C 8/0033 411/55 |

OTHER PUBLICATIONS

International Preliminary Report on Patentability for PCT/US2013/067858 mailed May 5, 2015.
Office Action from related EPO Application No. 13792797.6-1664 issued Mar. 23, 2017.

* cited by examiner

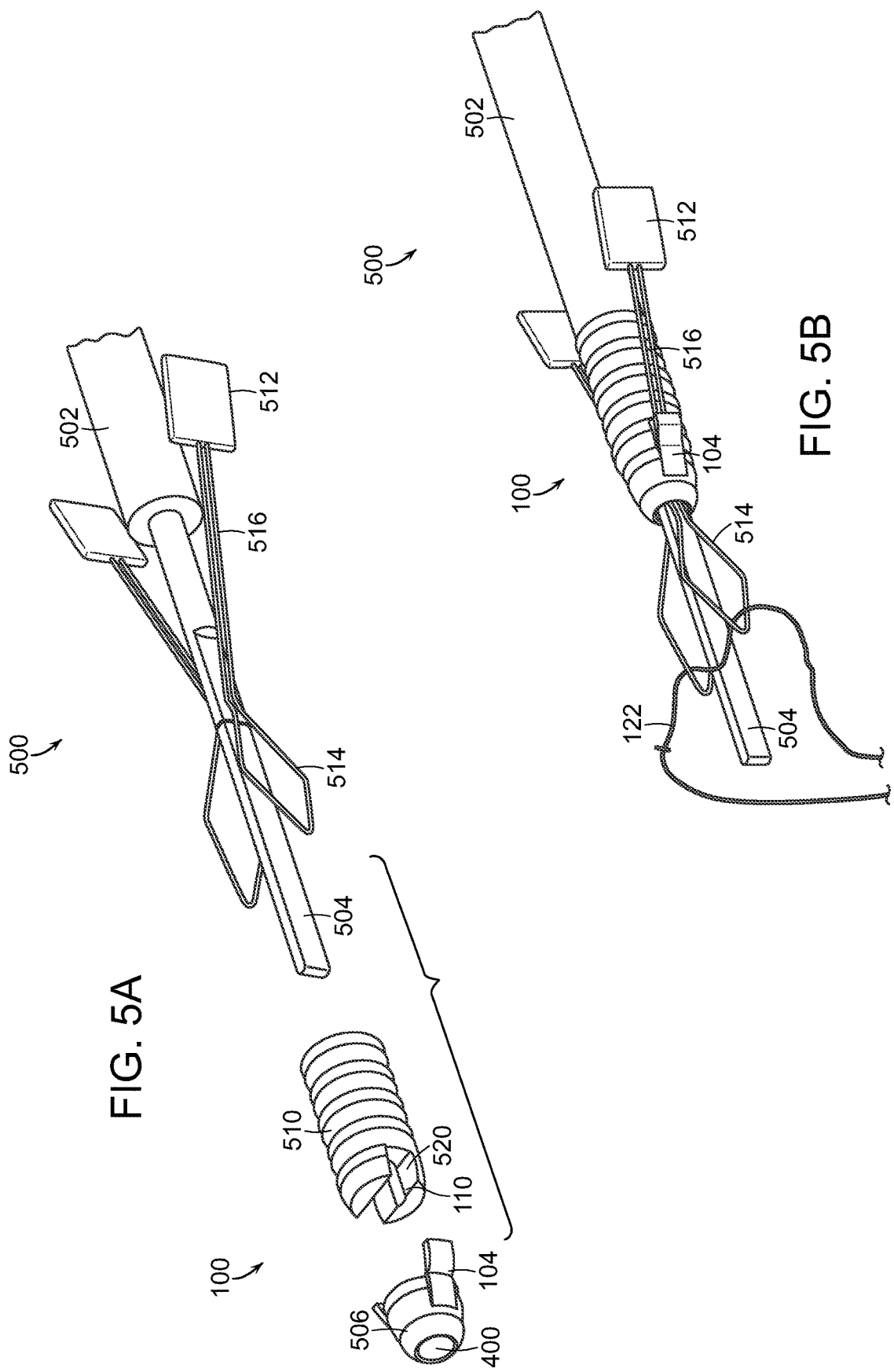

KNOTLESS ANCHOR

CROSS REFERENCE TO RELATED APPLICATIONS

This application is the U.S. national phase entry under 35 U.S.C. §371 of International Application No. PCT/US13/67858, filed Oct. 31, 2013, entitled KNOTLESS ANCHOR, which in turn claims priority to and benefit of U.S. Provisional Application No. 61/721,614, filed Nov. 2, 2012, which is incorporated herein by reference in its entirety for all purposes.

BACKGROUND

The labral tissue, or labrum, is a type of soft tissue or cartilage that surrounds the socket of ball-and-socket joints, such as the shoulder and the hip joints. The labrum forms a ring around the edge of the bony socket of the joint and helps to provide stability to the joint by deepening the socket. The labrum may further assist in containing lubricating fluids within the joint, promoting flexibility and motion.

Ball-and-socket joints may become damaged when experiencing high stresses. Often, joint damage may involve tearing of the labral tissue away from the underlying bone. This labral tearing may cause a patient to experience severe pain and give rise to abnormal motion of the ball-and-socket joint. Over time, such abnormal motion may lead to excessive cartilage wear within the joint and arthritis.

In most cases, once the labrum is torn from the bone, surgery is required to repair the damaged labrum. This surgery may involve reattachment of the torn labrum to the bone or attachment of a tissue graft to the damaged portion of the labrum. In either case, it is desirable to reduce the number of surgical implants and/or the number of steps required during surgical repair.

SUMMARY

Reconstructive surgery often employs surgical attachment techniques using a suture secured to a rigid skeletal member such as a bone. For example, labral reconstructive surgery often involves sutured reattachment of the labrum or tissue grafts to the circumference of a socket joint. Embodiments of the present disclosure relate to knotless suture anchors for use in surgical techniques, such as labral reconstructive repair.

For example, in an embodiment, a knotless suture anchor may include a generally elongated body having proximal and distal ends. In certain embodiments, the body includes a distal tapered tip and a uniform cross-section extending proximally from the distal tip. In alternative embodiments, the anchor body is tapered along its length, with the body cross-section becoming smaller towards the distal end. In further embodiments, the cross-sectional shape of the body is circular. In alternative embodiments, the cross-sectional shape of the body is ovoid.

The suture anchor may further include one or more wings that extend outward and proximally from the anchor body. In certain embodiments, the suture anchor may include a pair of wings, positioned on opposing faces of the suture anchor. In alternative embodiments, the suture anchor may include three, four or five wings.

The distal end of each wing may be secured to the anchor body at a distal end, while the proximal end of each wing may be free. The junction between the distal end of each wing and the anchor body may further include a hinge. The hinge allows the wings to pivot between an open position, where the proximal ends of the wings are distanced from the anchor body and a closed position, where at least a portion of the wings abut the anchor body. In certain embodiments, the wings may be biased in an open position.

A transverse bore may be further formed within the anchor body, extending through the suture anchor. The transverse bore may be dimensioned to receive a suture. When embodiments of the anchor are in use, a suture is passed through the transverse bore and the anchor may be positioned within a hole or recess formed in bone. So positioned, the one or more wings are urged from the open position into the closed position by contact with the sidewalls of the hole. Concurrently, at least a portion of the suture is compressed between the anchor body and the wings (e.g., the inner surface of the wings). Furthermore, the wings exert a compressive force upon the suture that inhibits sliding of the suture with respect to the anchor body.

In additional embodiments, grooves may be formed in the outer surface of the anchor body, corresponding to each wing, to further promote retention of the suture within the suture anchor. When positioned within the suture anchor, the suture may be routed within one or more of the grooves and the transverse bore. When the one or more wings are urged in the closed position, the inner surface of the wings may abut the suture along at least a portion of the length of the grooves. This configuration further increases the area of contact over which the suture is compressed between the anchor body (e.g., the grooves) and the wings (e.g., the inner surface of the wings) and further inhibits sliding of the suture with respect to the anchor body.

In an embodiment, each of the components of the anchor is formed from the same or different materials. In further embodiments, each of the components of the anchor is independently formed from biocompatible materials or a material with a biocompatible coating. Examples of biocompatible materials include, but are not limited to, biocompatible polymers, biocompatible metals, metal alloys, and metal oxides, and biocompatible ceramics and glass-ceramics. Examples of biocompatible polymers include, but are not limited to, thermoplastic polyurethanes (e.g., polyester-based polyurethanes, polyether-based urethanes, and polycarbonate-based polyurethanes, in aromatic or aliphatic grades), polyamides, fluoropolymers, polyolefins, and polyimides. Specific examples of biocompatible polymers may include polyether ether ketone (PEEK), polytetrafluoroethylene (PTFE), polyvinyl chloride (PVC), and nylons. Examples of biocompatible metals include, but are not limited to, titanium, titanium alloys (e.g., $Ti_6Al_4$, $Ti_6Al_4V$, $Ti_6Al_7Nb$), CoCrMo, stainless steel (e.g., 316L). Examples of biocompatible ceramics include, but are not limited to, diamond-like carbon (DLC), aluminum oxide, calcium phosphates, zirconium oxide. In a preferred embodiment, the anchor is formed from one or more of PEEK, titanium, and a biocomposite material (e.g., Regensorb, Smith & Nephew, PLC, London, UK).

In an embodiment, the distal tip of the anchor is formed from a different material than the body of the anchor. For example, the tip may be formed from titanium, while the anchor body is formed from a biocompatible polymer or ceramic.

In an embodiment, a suture anchor is provided. The suture anchor includes an elongated body and a transverse bore through the body. The suture anchor further includes a wing hingedly attached to the body at one end in the distal region of the anchor body.

Additional embodiments of the suture anchor include one or more of the following, alone or in combination. For example, the suture anchor includes at least one longitudinally extending groove formed in the outer surface of the body and extending along at least a portion of the length of the body, where the distal end of the wing is hingedly attached to a distal end of the groove. The suture anchor includes a second groove and a second wing, where a distal end of the second wing is hingedly attached to a distal end of the second groove. Optionally, the second groove and the second wing are positioned at diametrically opposed surfaces of the body to the first groove and wing. The hinge of the suture anchor is formed integrally with the anchor body, optionally a living hinge. Optionally, the transverse bore connects the at least one groove. Each wing further includes at least one protrusion on an inner surface. Optionally, the at least one protrusion is positioned adjacent the transverse bore, such that at least a portion of the protrusion extends into the transverse bore, in use. This arrangement helps to provide enhance fixation of the suture within the anchor. The suture anchor includes an anchor body including a first plurality of circumferential ribs. Optionally, the outer surface of each wing includes a second plurality of ribs corresponding to the first plurality of ribs. The suture anchor includes an anchor body including a longitudinal bore extending through at least a portion of the anchor body. Optionally, the longitudinal bore extends into the transverse bore. In further embodiments, the longitudinal bore extends fully through the anchor body.

In an embodiment, the groove is dimensioned to mate with its corresponding wing. For example, the width, length, and depth of the mating groove is about equal to the width, length, and thickness of its corresponding wing and the wing is fully seated within the groove when urged into contact with the anchor body. In a further embodiment, when the wing is positioned within its mating groove, the second plurality of ribs abut the first plurality of ribs and forms a plurality of ribs extending continuously about the outer surface of the anchor.

In an additional embodiment, the groove is dimensioned to mate with its corresponding wing along only a portion of the length of the anchor body. For example, the width and depth of the wing and its mating groove are equal, while the length of the groove is less than the length of the wing.

In an alternative embodiment, the groove is dimensioned to fully receive its corresponding wing along only a portion of the length of the anchor body. For example, the width of the wing and its mating groove are equal, while the depth of the groove is different than the length of the wing along a selected portion of the length of the anchor. The divergence between the depth of the groove and the thickness of the wing may begin at the distal end of the wing or at a location proximal to the distal end of the wing. The divergence between the depth of the groove and the thickness of the wing may be accomplished by decreasing the groove depth with respect to the wing thickness or increasing the wing thickness with respect to the groove depth. In either case, the divergence between the depth of the groove and the thickness of the wing causes the outer surface of the wing extends outside the groove.

In a further embodiment, a suture anchor is provided. The suture anchor includes an elongated anchor body. The suture anchor also includes at least one longitudinally extending groove formed along at least a portion of the outer surface of the anchor body. The suture anchor additionally includes a transverse bore extending through the anchor body and in communication with the at least one groove. The suture anchor also includes a wing extending from the at least one groove, where the at least one groove is dimensioned to receive the wing. The suture anchor further includes a hinge attaching the wing with the anchor body and permitting motion of the wing between a first position, where the wing extends outside of its corresponding groove, and a second position, where at least a portion of the wing is positioned within its corresponding groove.

In an embodiment, a segmented suture anchor is provided. The segmented suture anchor includes an elongate body formed in two pieces, a distal anchor body and a proximal anchor body. A longitudinal bore extends through each of the proximal and distal anchor bodies. The proximal anchor body further includes a transverse bore extending through the proximal anchor body and positioned adjacent a distal end of the proximal anchor body. The distal anchor body further includes one or more wings extending from an outer surface thereof, the one or more wings being positioned adjacent to the transverse bore of the proximal anchor body in an assembled configuration of the anchor.

In an additional embodiment, a method of inserting a suture anchor in a structure is provided. The method includes providing a suture anchor having an elongate body. The elongate body is formed from two pieces, including a distal anchor body and a proximal anchor body separate from one another. A longitudinal bore extends through each of the proximal and distal anchor bodies, such that the assembled elongate anchor body is cannulated. The proximal anchor body further includes a transverse bore which is located in a distal region of, and extends through, the proximal anchor body. The distal anchor body includes one or more wings extending from an outer surface thereof, the one or more wings being positioned adjacent to the transverse bore of the proximal anchor body in an assembled configuration. The method further includes inserting one or more wire loops through the longitudinal bore at a proximal end of the proximal anchor body, where the one or more wire loops are dimensioned to receive a suture. The method also includes advancing the wire loops through the longitudinal bore until at least a portion of the wire loops exit the distal end of the distal anchor body. The method further includes inserting a suture through at least one of the wire loops. The method also includes retracting the wire loops through the longitudinal bore of the distal anchor body and at least one end of the transverse bore of the proximal anchor body, where the ends of the suture exit the anchor body through at least one end of the transverse bore. The method additionally includes advancing the suture anchor into a recess, the recess having a diameter smaller than the one or more wings, where the recess urges the wings into frictional engagement with the suture by compression of the wings against the recess.

Additional embodiments of the method include one or more of the following. For example, inserting a suture through at least one of the wire loops includes inserting a first end of the suture through a first wire loop and inserting a second end of the suture through a second wire loop. After retracting the wire loops, the first end of the suture exits the anchor body through a first end of the transverse bore and the second end of the suture exits the anchor body through a second end of the transverse bore. Inserting a suture through at least one of the wire loops includes inserting each end of the suture through a single wire loop. After retracting the wire loops, each end of the suture exits the anchor body through a single end of the transverse bore. Inserting a suture through at least one of the wire loops includes inserting each end of the suture through a first and a second wire loop. After retracting the wire loops, each end of the suture enters the anchor body through a first end of the transverse bore and each end of the suture exits the anchor body through a second end of the transverse bore.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIGS. 5A-5C are schematic illustrations of a segmented knotless suture anchor and an insertion tool for use in conjunction with embodiments of the segmented knotless suture anchor.

DETAILED DESCRIPTION

Figure 1A:
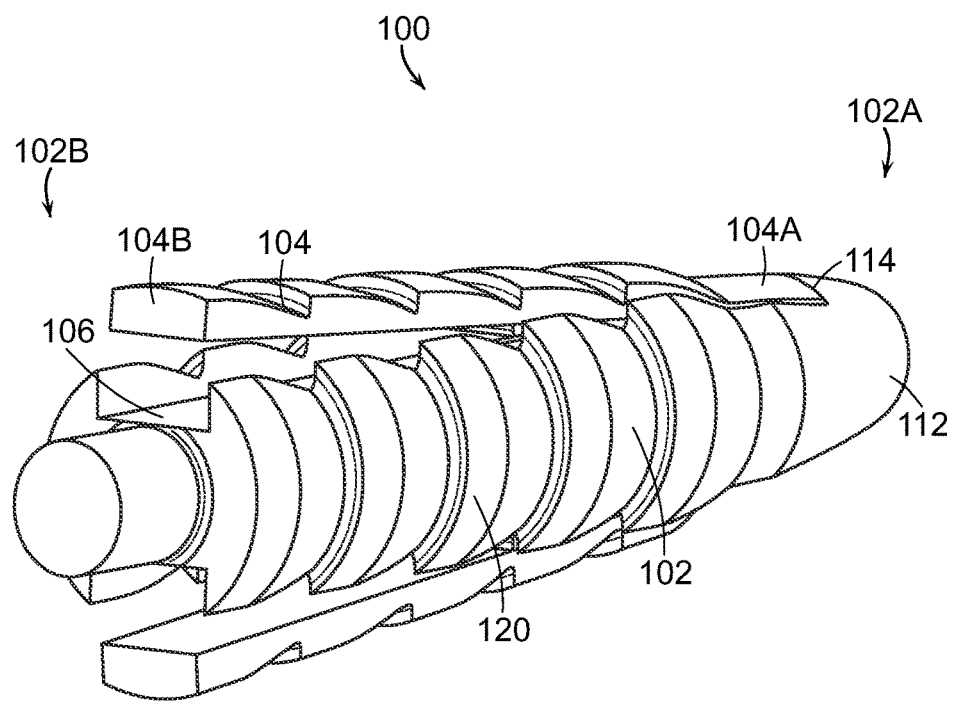
FIGS. 1A-1D are schematic illustrations of an embodiment of the knotless suture anchor of the present disclosure; (A) perspective view; (B) cutaway view; (C) open configuration; (D) closed configuration.
Figure 1B:
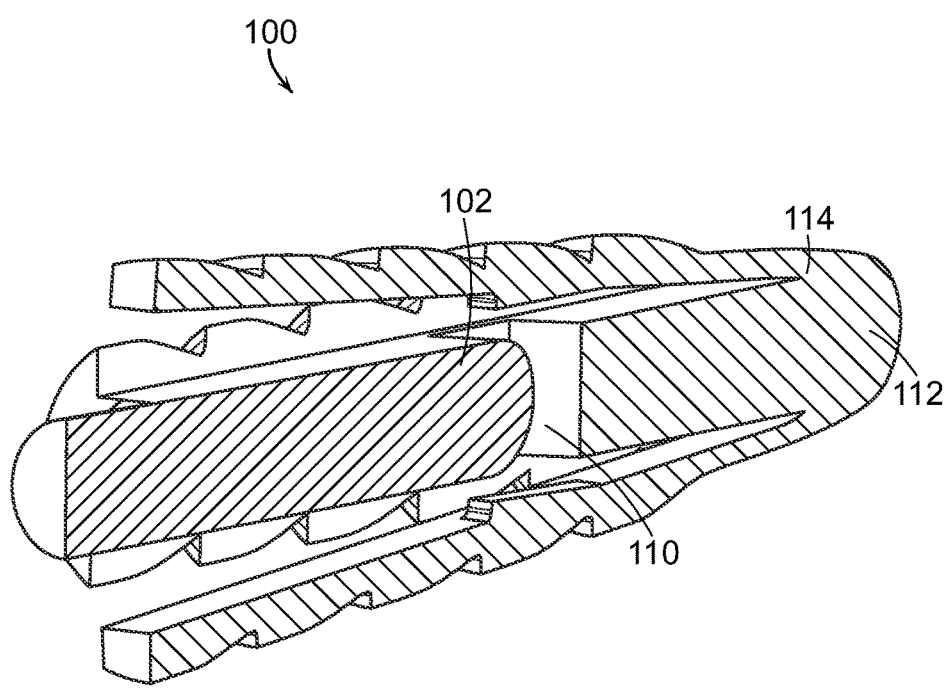
Figure 1C:
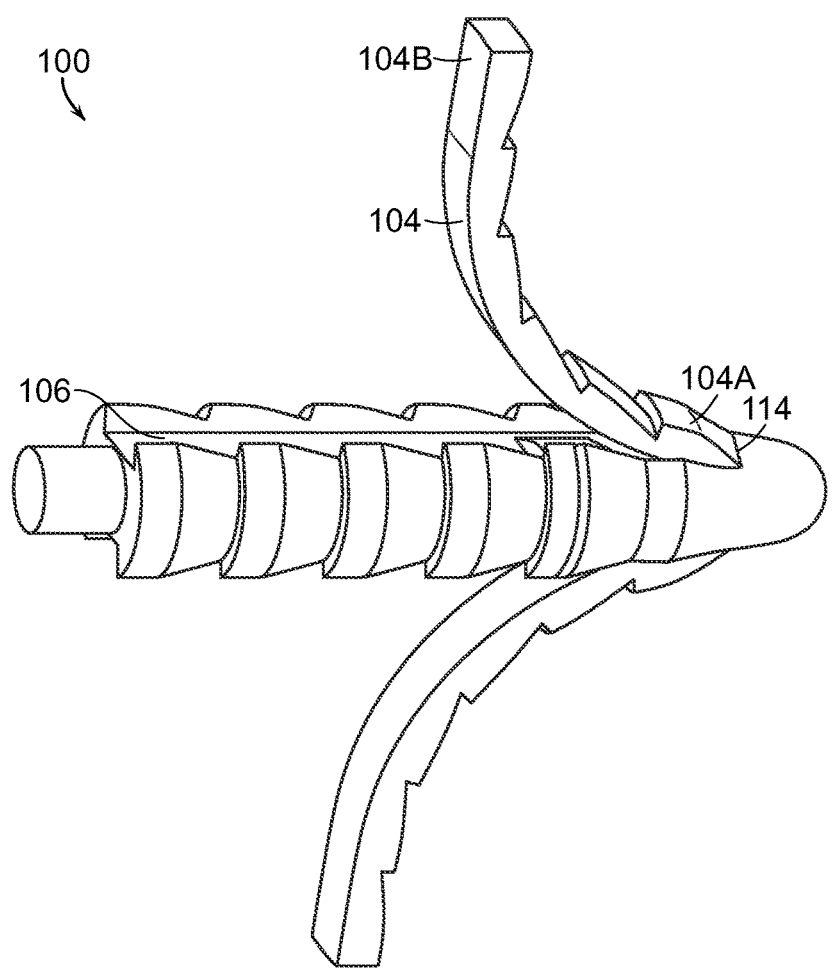

Specific embodiments of a suture anchor will now be described with reference to the Figures. According to FIGS. 1A-1D, there is illustrated a first embodiment of a knotless suture anchor 100. The suture anchor 100 includes a body 102, one or more wings 104, and a transverse bore 110. The suture anchor 100 further includes grooves 106. In alternate embodiments, not shown, the anchor body does not include grooves in its outer surface.

The body 102 is generally elongate and includes distal and proximal ends 102A, 102B, respectively, and a tip 112 positioned at about the distal end 102A (e.g., a tapered tip). In the illustrated embodiments, the cross-section of the body 102 from the proximal end 102B to the distal end 102A, through the distal tip 112, is generally circular in shape and tapered, where the cross-sectional area decreases from the proximal end 102B to the distal end 102A. In an alternative embodiment, the body includes a tapered distal tip and the cross-section of the body, extending proximally from the distal tip, is approximately uniform in dimension. In further embodiments, the cross-sectional shape of the body is ovoid.

Figure 1D:
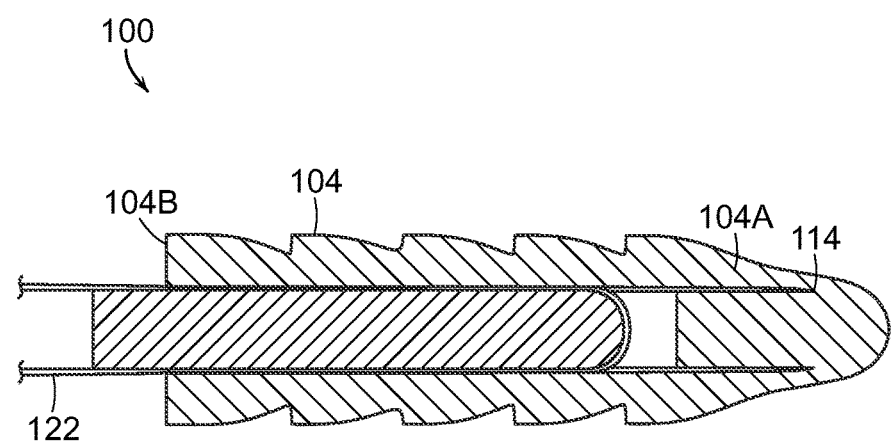
Figure 2A:
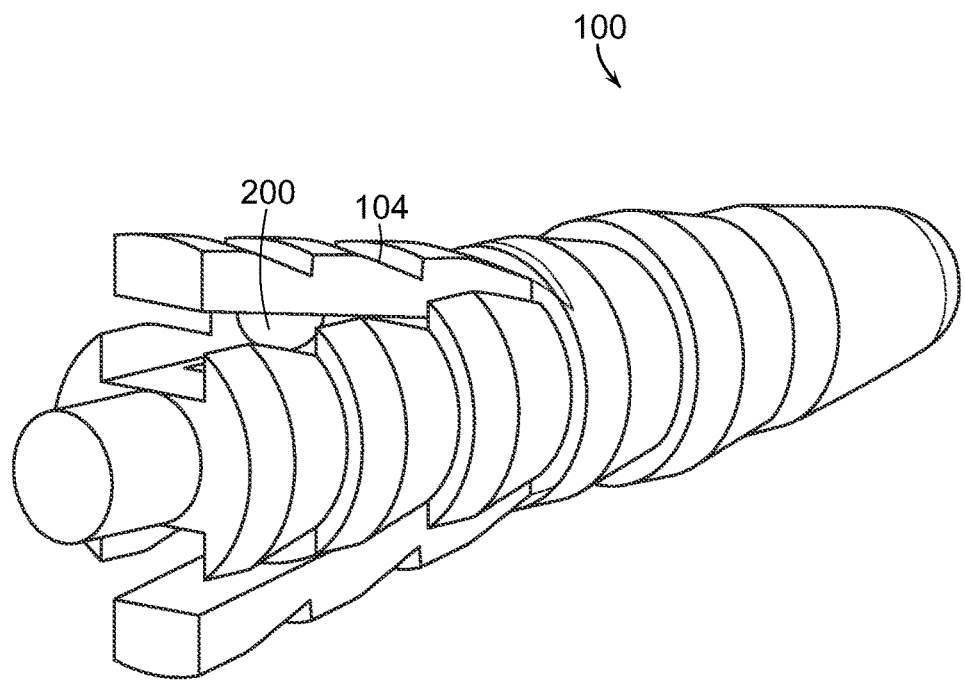
FIGS. 2A-2D are schematic illustrations of an embodiment of a knotless suture anchor including an inner wing protrusion; (A) perspective view; (B) cutaway view; (C) open configuration; (D) closed configuration.
Figure 2B:
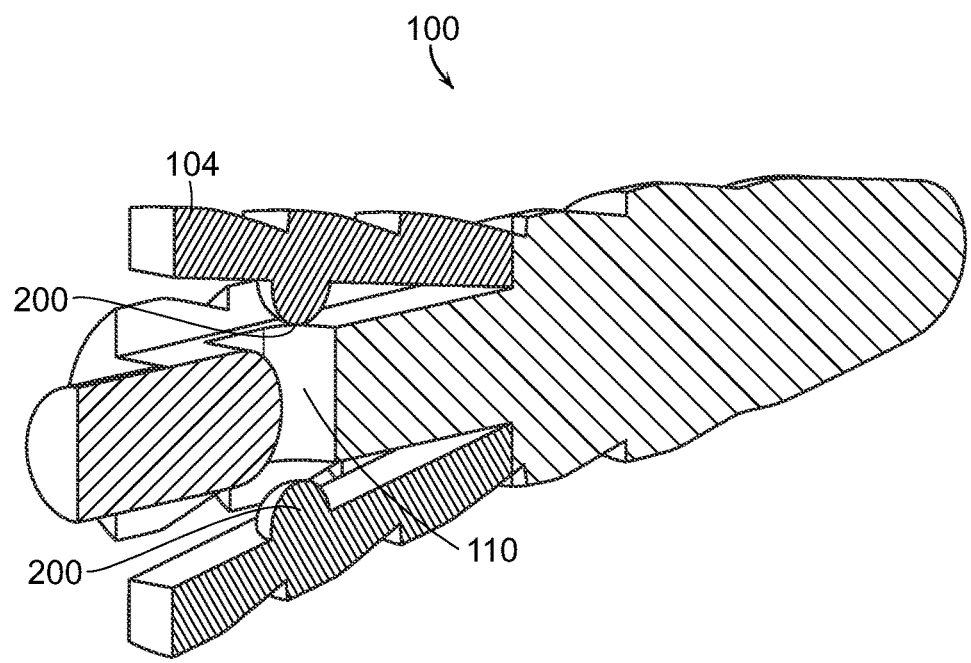
Figure 2C:
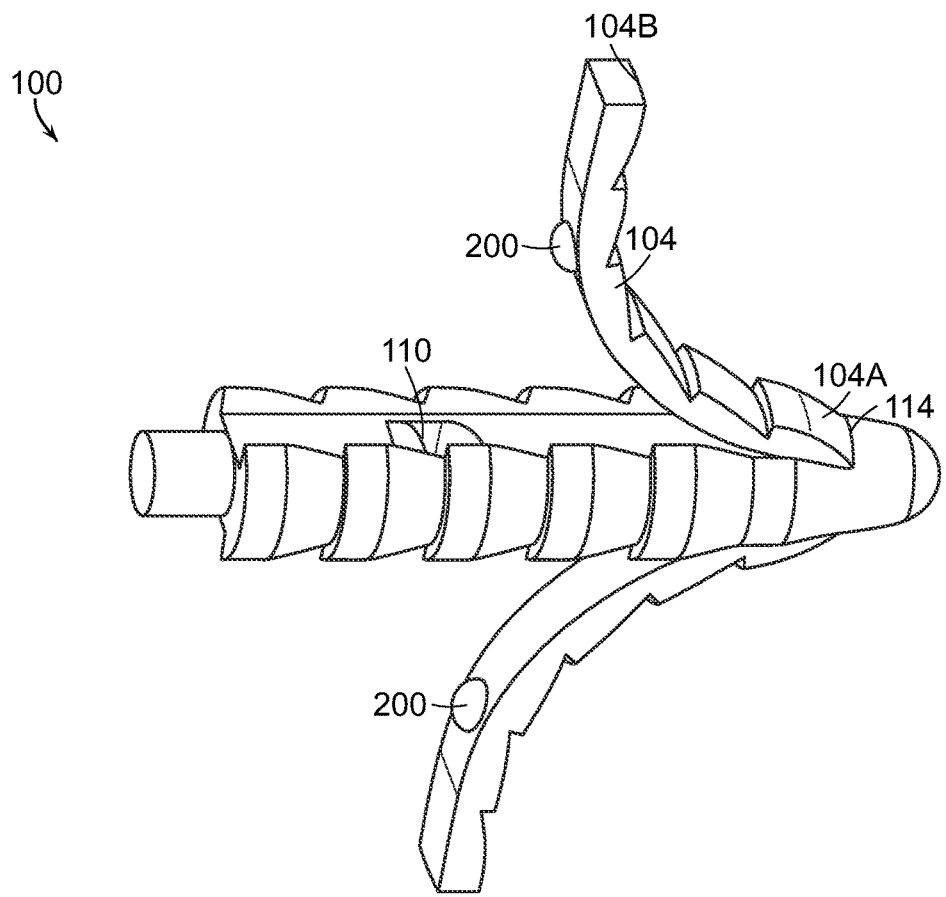
Figure 2D:
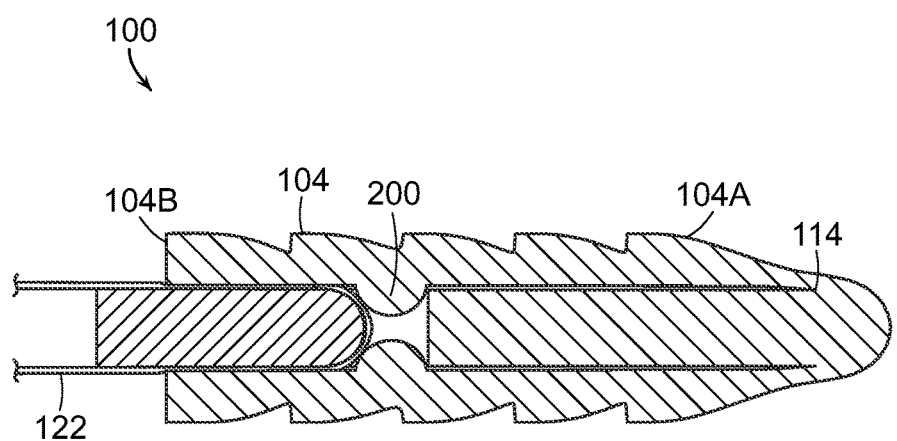

The suture anchor 100 further includes a transverse bore 110 extending laterally through the anchor body 100. The ends of the transverse bore 110 allow entry of the suture into the transverse bore 110. In certain embodiments, the transverse bore 110 is positioned along the length of the anchor body such that it intersects one or more of the grooves 106. With the suture anchor 100 so configured, a suture 122 may be routed through the transverse bore 110 and one or more of the grooves 106 (e.g., two grooves), as illustrated in FIG. 1D.

The one or more wings 104 are generally elongate and attached to the anchor body 102 at a distal end 104A. The wings 104 are each offset from the terminus of the distal end 102B (e.g., by the distal tip 112) and extend proximally from their point of attachment with the anchor body 102. In certain embodiments, the length of each wing may be dimensioned so as to extend to the proximal end of the anchor body. In other embodiments, the length of each wing may extend a shorter distance, terminating prior to the proximal end of the anchor body.

In the illustrated embodiments, the suture anchor 100 includes a pair of wings 104 and corresponding grooves 106. The pair of wings 104 and grooves 106 are positioned on opposing surfaces of the anchor body 102. However, it may be understood that the number of wings and grooves may be increased or decreased, as necessary. In an alternative embodiment, the anchor may include a single wing. In further embodiments, not shown, the anchor may include more than two wings (e.g., three, four, five, etc.). Furthermore, the wings may be positioned at any positions about the periphery of the anchor body, without limit.

A hinge 114 attaches each of the wings 104 to the body 102. In the illustrated embodiment, the hinge 114 is a live hinge, integrally formed with the anchor body 102 and its respective wing 104. Each hinge 114 allows its respective wing 104 to pivot between an open position, where the wing 104 extends outward from the anchor body 102 (FIG. 1C), and a closed position, where at least a portion of the wing 104 proximal to the anchor 114 abuts the anchor body 102 (FIG. 1D).

In alternative embodiments, not shown, the wings and anchor body are formed separately. For example, the distal end of a wing is attached to the anchor body, where the distal end of the wing attached to the anchor body forms the hinge. In another example, the hinge may be formed separately from each of the wings and the anchor body and attached to each wing and the anchor body (e.g., an elastic material). In either case, such attachment may be formed by use of an adhesive or mechanical fixation device (e.g., rivets, screws, and the like).

The one or more grooves 106 are formed in the outer surface of the anchor body 102, in a region adjacent to and corresponding with the wings 104. That is to say, a groove 106 is formed for each wing 104 present in the anchor 100. In the embodiments illustrated in FIGS. 1A-4B, each of the one or more grooves 106 extend proximally from the hinge 114 and possesses a length approximately equal to the length of its corresponding wing 104. For example, each of the grooves 106 extends from a corresponding hinge 114 to the proximal end of the anchor body 102B. In alternative embodiments, the length of each groove may be greater than or shorter than the length of its corresponding wing. In further alternative embodiments, not shown, the grooves may be omitted.

The grooves 106 are dimensioned such that an outer surface of a corresponding wing is substantially flush with the outer surface of the anchor body 102 when the wing is in the closed position. That is to say, the depth of each of the grooves 106 is approximately equal to the thickness of its respective wing 104. In further embodiments, the width of each of the grooves may be approximately equal to the thickness of its respective wing. As discussed in greater detail below, dimensioning the grooves to complement the shape of the wings facilitates frictional retention of sutures within embodiments of the suture anchor. In alternative embodiments, the depth of each of the grooves is independently selected to be greater than or less than its corresponding wing.

Figure 5C:
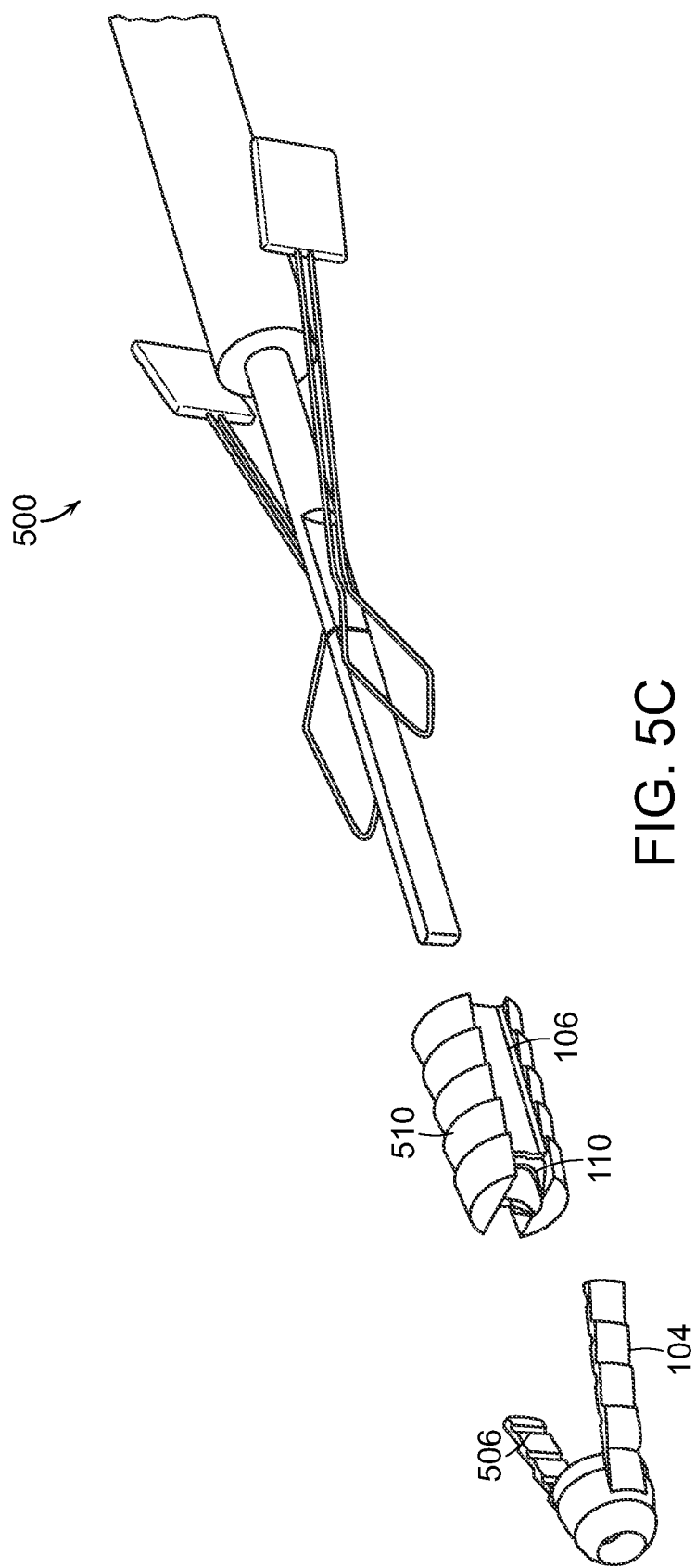

In an alternative embodiment, discussed with respect to FIG. 5A-5C, the suture anchor 100 is formed in two pieces, a distal anchor body 506 and a proximal body 510. The distal body 510 includes a distal tip 112 and wings 104. The proximal body 506 includes a transverse bore 110. The segmented configuration of the anchor 100 helps to facilitate loading the anchor 100 with a suture, as discussed in greater detail below.

In a surgical application employing the suture anchor 100, a surgical recess is drilled in a body (e.g., a bone) such that the recess has a diameter smaller than the anchor. Accordingly, insertion of the suture anchor 100 into the recess urges the wings 104 into frictional engagement with the suture 122 by compression of the wings 104 against the recess, inhibiting removal of the suture 116 from the anchor 100. Typically a drilled hole provides a circular recess of a consistent diameter that is well suited for retaining the anchor 100. However other types of surgical recesses may be employed. Pivoting of the wings 104 about the hinge 114 from the open position to the closed position therefore brings the wings 104 into alignment with the anchor body 102 as the wings 104 are received into their respective grooves 106.

To facilitate retention of the anchor 104 within the bone, the anchor body 102 may further include a plurality of ribs 120 extending about the periphery of the anchor body 102. The ribs 120 are generally spaced apart from one another along the length of the anchor body 102, between the distal and proximal ends 102A, 102B, as illustrated in FIGS. 1A-1D. Alternatively, the ribs may be formed in a helical configuration, extending continuously between the distal and proximal ends. When the anchor 100 is placed within a surgical recess, such as a hole drilled through bone, the ribs 120 encounter greater compressive force from the surrounding recess, and the resilient nature of the anchor material allows a slight deformation for conforming the ribs in the recess, and may be continuous with the outer surface of the wings 104.

FIGS. 2A-4E present schematic illustrations of alternative embodiments of a knotless suture anchor. With respect to FIGS. 2A-2D and 3A-3B, the suture anchor of FIG. 1 has been modified to include protrusions 200 on inner surfaces of one or more of the wings 104. The protrusions 200 are positioned to align with and enter the transverse bore 110 when the wings 104 are in the closed position. So configured, the wings provide additional frictional engagement with suture 122 positioned within the transverse bore 110, further inhibiting removal of the suture 122 from the suture anchor 100.

Figure 3A:
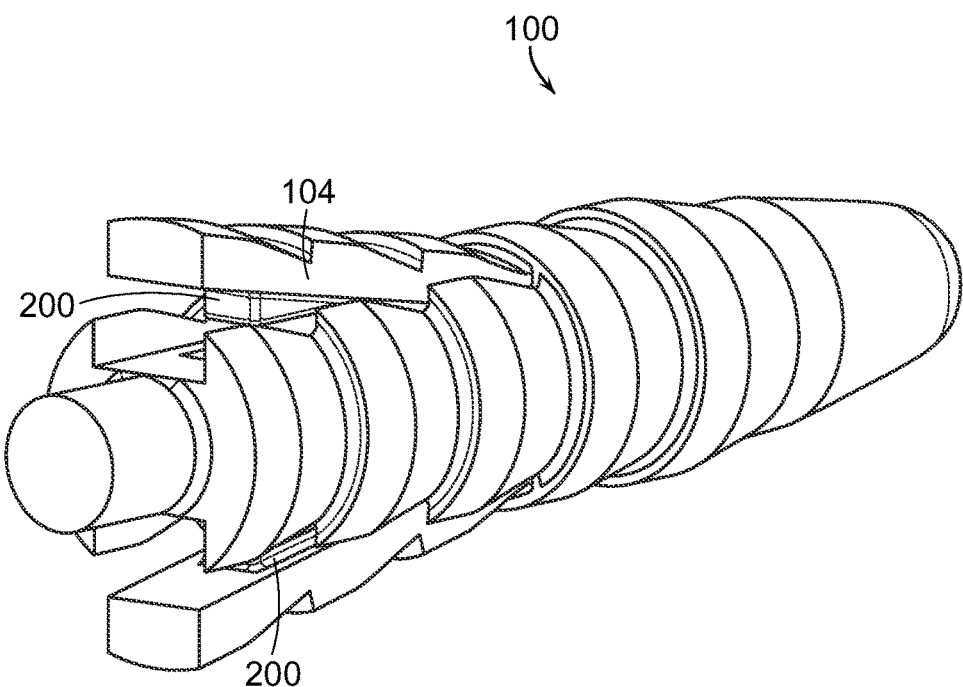
FIGS. 3A-3B are schematic illustration of an embodiment of a knotless suture anchor including a proud surface on an inner wing for securing a suture.
Figure 3B:
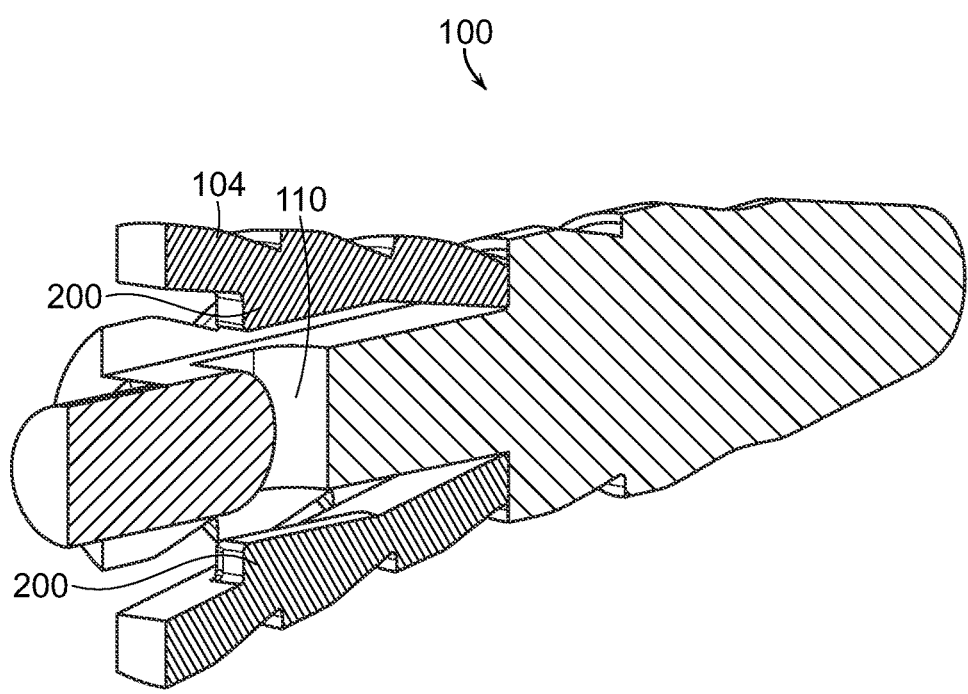

The protrusions may adopt any shape, provided that it fits within the transverse bore 110. For example, the protrusions may adopt a hemispherical shape, as illustrated in the embodiments of FIGS. 2A-2D or a rectangular shape, as illustrated in the embodiments of FIGS. 3A-3B.

In a further alternative embodiment, not illustrated, at least one inner surface of the one or more wings may be patterned or textured. Such feature may further increase the frictional sliding resistance of a suture with respect to the inner surface of the wing and enhance fixation of the suture with respect to the anchor.

Figure 4A:
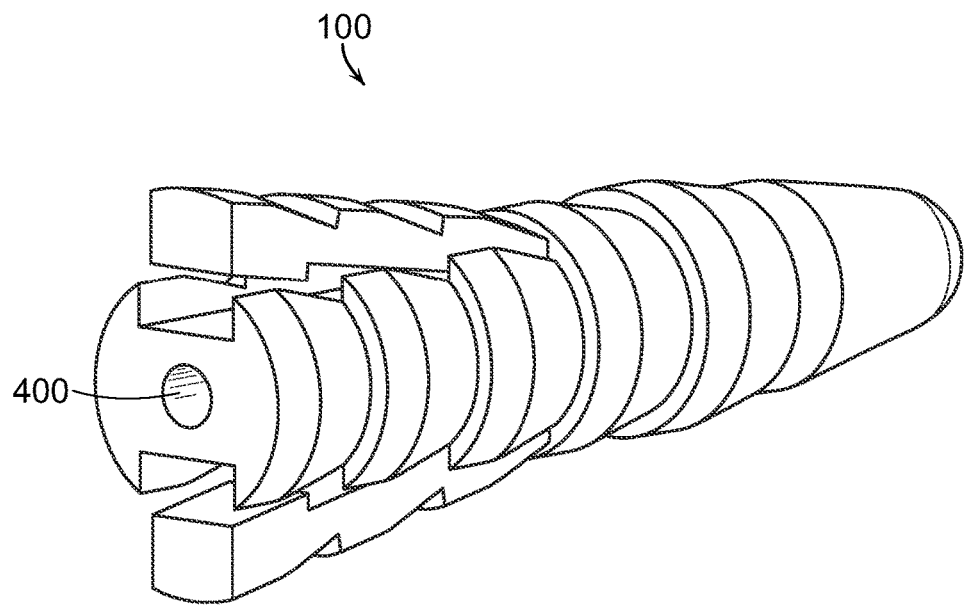
FIG. 4A is a schematic illustration of an embodiment of a knotless suture anchor including a longitudinal bore for insertion or communication with a transverse bore.

FIG. 4A illustrates an embodiment of the suture anchor 100 which includes a longitudinal bore 400. In an embodiment, the longitudinal bore 400 extends through the anchor body to intersect the transverse bore. In alternative embodiments, the longitudinal bore may terminate at a position proximal to the transverse bore. In further embodiments, the longitudinal bore extends fully through the anchor body. As shown, the longitudinal bore 400 is concentric with a longitudinal axis of the suture anchor 100 and possesses a circular cross-section. In further embodiments, the cross-sectional shape of the longitudinal bore may be non-circular. Examples may include, but are not limited to, ovoid and closed-sided, faceted surfaces (e.g., triangle, square, polygon, etc.). As discussed in greater detail below, the longitudinal bore may facilitate engagement of the anchor with an inserter tool. For example, the longitudinal bore may receive a portion of a delivery tool, allowing the anchor to be positioned by manipulation of the tool.

Figure 4B:
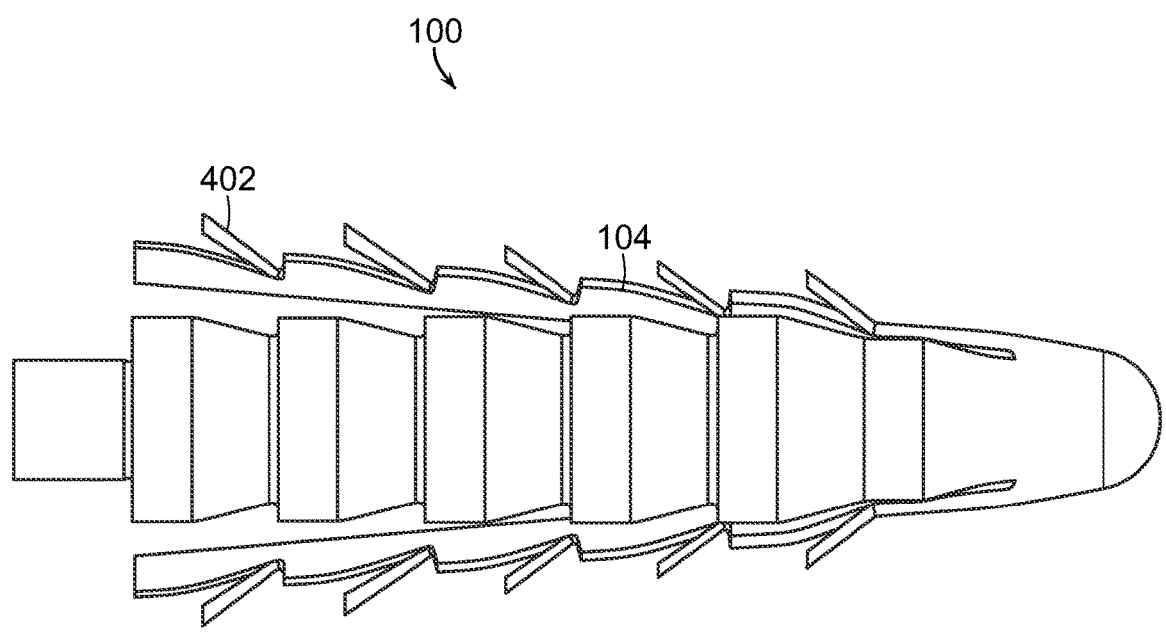
FIG. 4B is a schematic illustration of an embodiment of a knotless suture anchor including a wing-on-wing configuration.

FIG. 4B illustrates an embodiment of a suture anchor which includes secondary wings 402 mounted on wings 104. The secondary wings 402 provide increased fixation between the anchor 100 and the bone hole into which the anchor 100 is inserted.

Figure 4C:
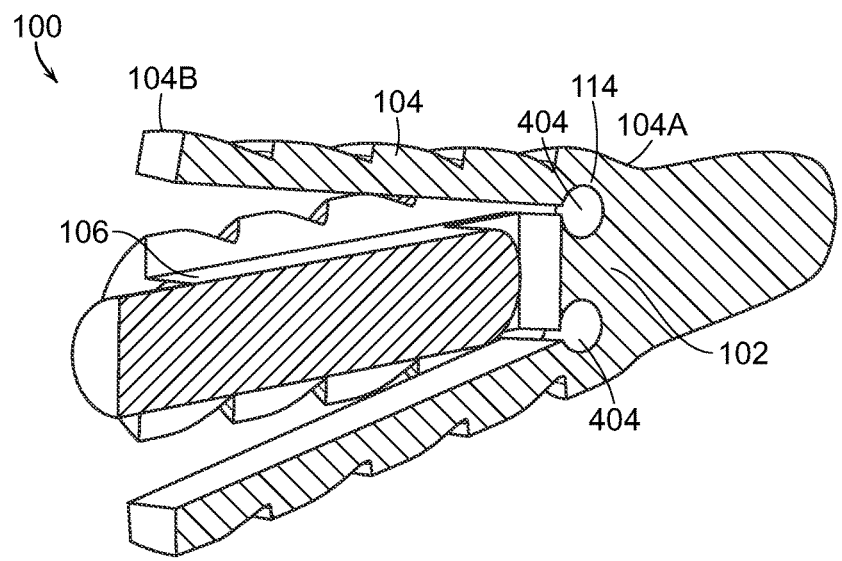
FIGS. 4C-4D are schematic illustrations of embodiments of knotless suture anchors including stress relieving features

FIG. 4C illustrates an embodiment of a suture anchor which has been modified with respect to the suture anchor 100 of FIG. 1A-1D to remove possible stress concentrating features which can result in crack growth and fracture. In general, when two surfaces come together at vertex (e.g., a crack-like shape), a remotely applied stress is magnified near the sharp tip. In contrast, two surfaces joined at a curved surface do not concentrate stress to the same degree. To help mitigate potential stress concentrations, the illustrated hinge 114 is formed with a curved junction between the anchor body 102 and the wings 104 (e.g., a circular junction), rather than a sharp or crack-like junction.

Figure 4D:
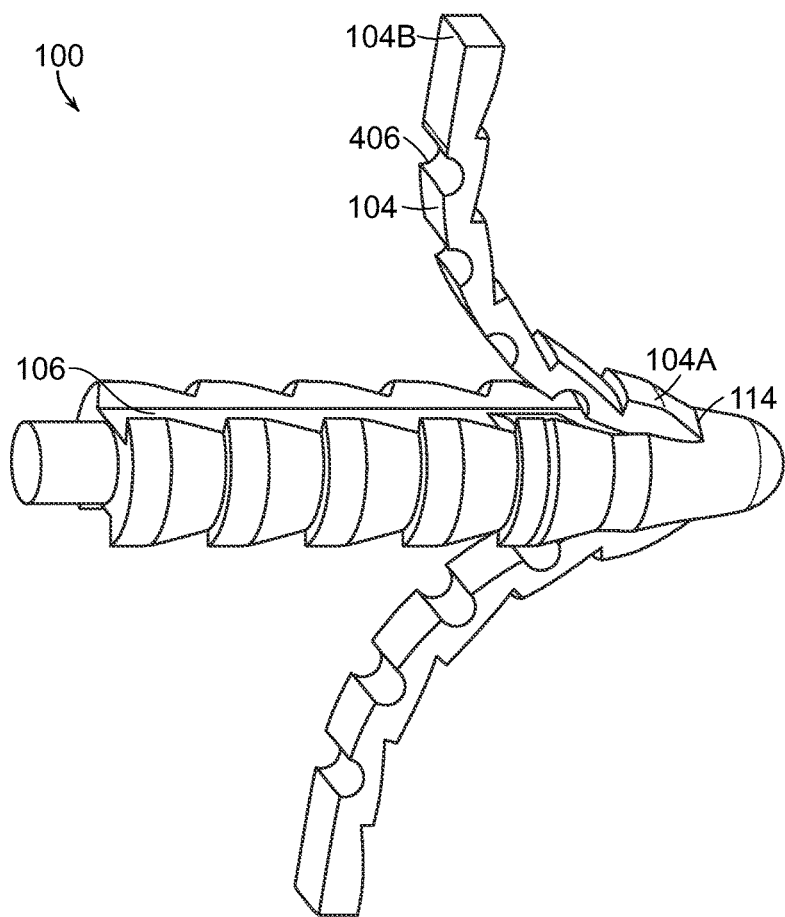

FIG. 4D illustrates an embodiment of a suture anchor which includes a plurality of notches 406 along the length of the wings 104. The notches 406 are positioned along the surface of the wings 104 and abut the anchor body 102 when the wings 104 are compressed (e.g., when the anchor 100 is positioned in a bone recess). Alternatively, the notches may be formed in the outer surface of the wings or a combination of the inner and outer surfaces. The notches act to relieve bending stresses which arise in the wings, inhibiting crack growth, fracture, and ultimate failure of the wing.

Figure 4E:
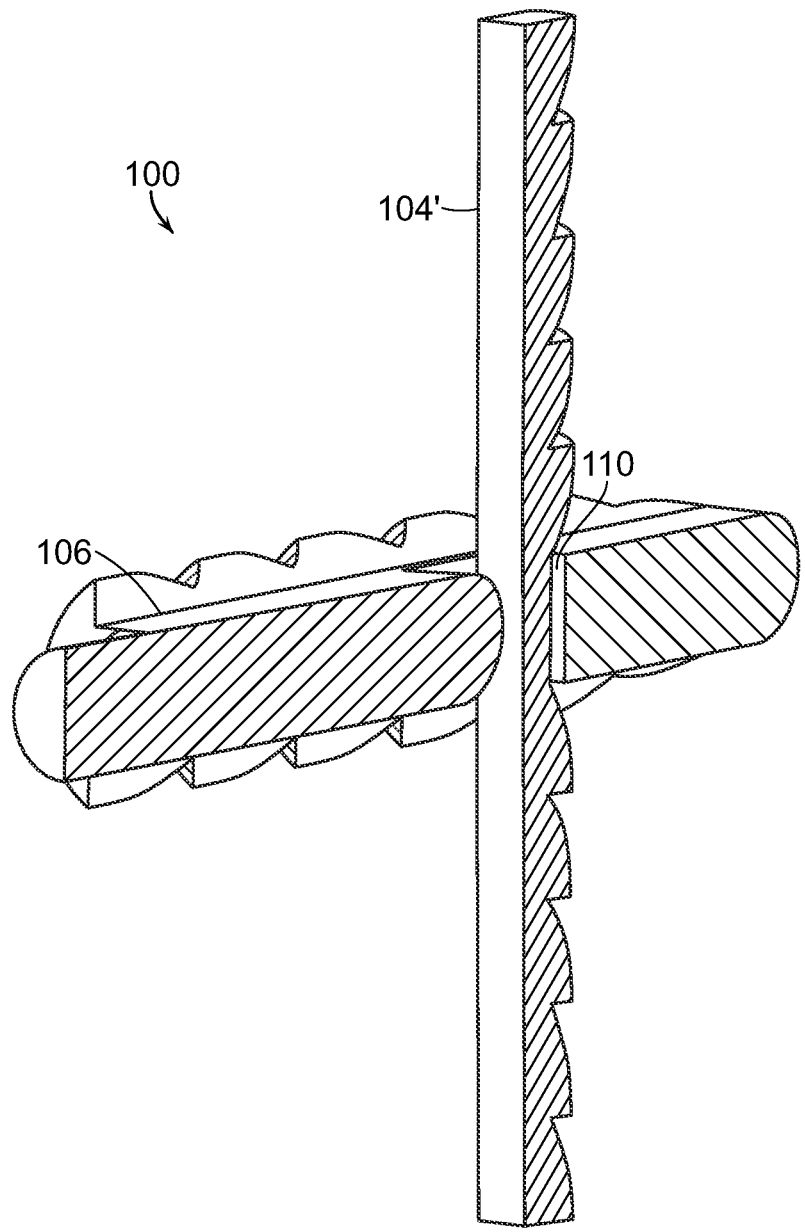
FIG. 4E is a schematic illustration of an embodiment of a knotless suture anchor including a wing insert.

FIG. 4E illustrates an alternative embodiment of a suture anchor which includes wings 104' that are inserted within the transverse bore 110, rather than mounted to the outer surface of the anchor body 102. The wings 104' may be combined with embodiments of the suture anchor 100 that include mating grooves 106, as discussed above, or with embodiments of suture anchor 100 that do not include grooves 106.

The discussion will now turn to FIGS. 5A-5E, which illustrates embodiments of an insertion tool 500 for use in loading a suture 122 within the suture anchor 100 and delivering the suture anchor 100 to a desired location. The inserter 500 includes a handle 502 and a shaft 504. The shaft 504 extends distally from the handle 502 and engages the anchor 100 by insertion through its longitudinal bore 400. In alternative embodiments, not shown, the tool and anchor may be modified such that the anchor is inserted within the shaft.

In further embodiments, the longitudinal bore can extend through the entire length of the anchor body. Also, the anchor can be segmented into a distal portion and a proximal portion. The distal portion may include the distal tip and the one or more wings, while the proximal portion may include the transverse bore and grooves, if present.

With reference to FIG. 5A, the inserter tool 500 includes wire loops 512 for retaining the suture 122. The wire loops 512 include a distal loop portion 514 and a proximal extension portion 516. The wire loops 512 are attached to the shaft 504, where the loop portion 514 extends outward from the shaft 504 distally, while the extension portion 516 extends outward from the shaft 504 proximally, with respect to an attachment point 518. In certain embodiments, the wire loops 512 may be provided in the same number and relative position as the wings 104. For example, as illustrated in FIGS. 5A-5C, the inserter tool 500 includes two opposed wire loops 512.

In use of the tool 500, the wire loops 512 are inserted through the longitudinal bore 400 of the anchor 100. The distal loop portion 514 is formed from a flexible material capable of reversibly deforming for travel through the bore 400. Suitable materials include, but are not limited to, nickel-titanium alloys (i.e., nitinol) and stainless steel. When the distal loop portion 512 is advanced through the longitudinal bore 400, the distal loop portion 514 extends out from a distal end of the distal anchor portion 506, while the proximal extension portion 516 extends outwards from the proximal anchor portion 510 through ends 520 of the transverse bore 110.

Subsequently, wire loops 512 are withdrawn from the anchor 100 to draw the suture 122 into engagement with the transverse bore 110. The extension portions 514 are drawn proximally through the ends 520 of the transverse bore 110 of the proximal anchor body 510. This motion also urges the distal loop portion 512 and the ends of the suture 122 through the distal anchor body 506 and ends 520 of the transverse bore 110. The manner in which the suture 122 is positioned within the wire loops 512 will determine how the suture is routed through the anchor body 100 as discussed in greater detail below.

Figure 6A:
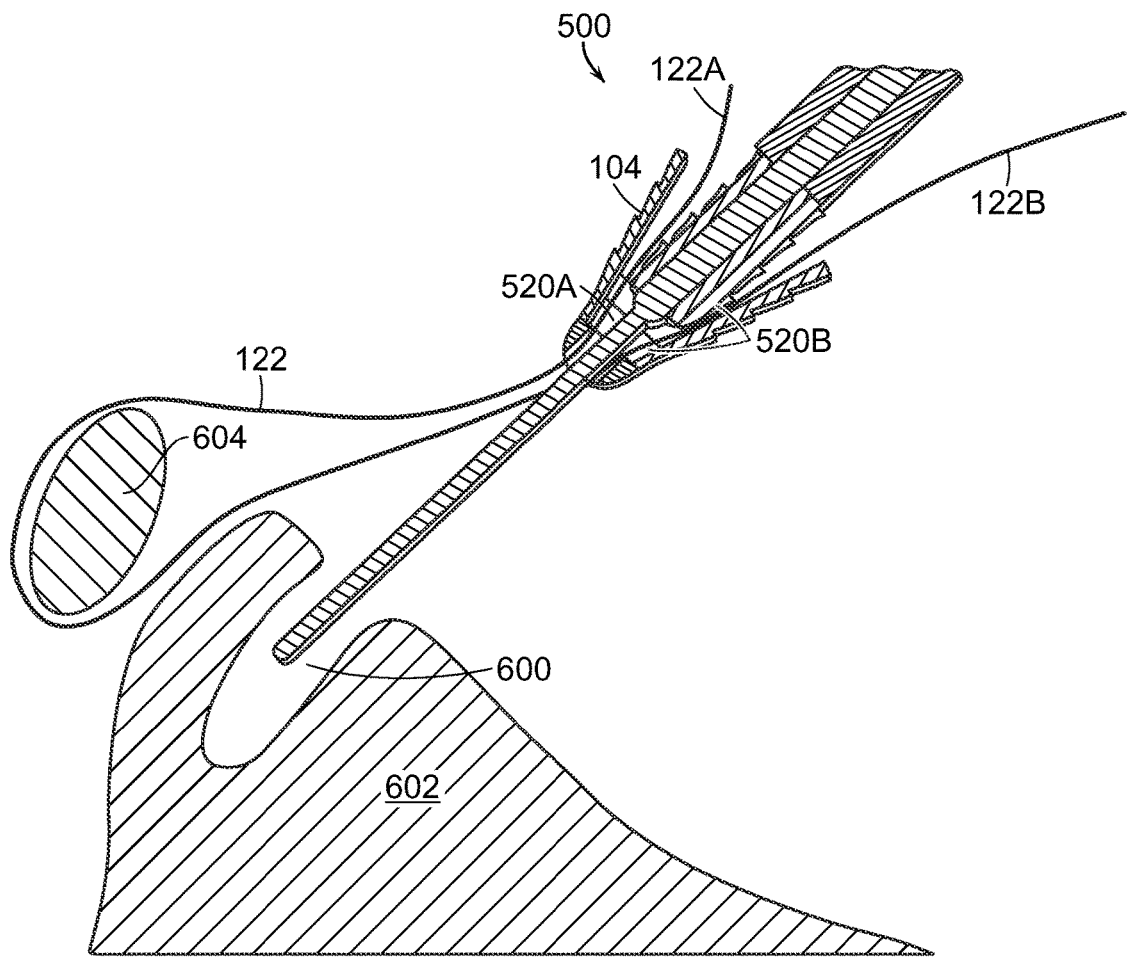
FIGS. 6A-6C are schematic illustrations of suture routing pathways through embodiments of the knotless suture anchor.
Figure 6B:
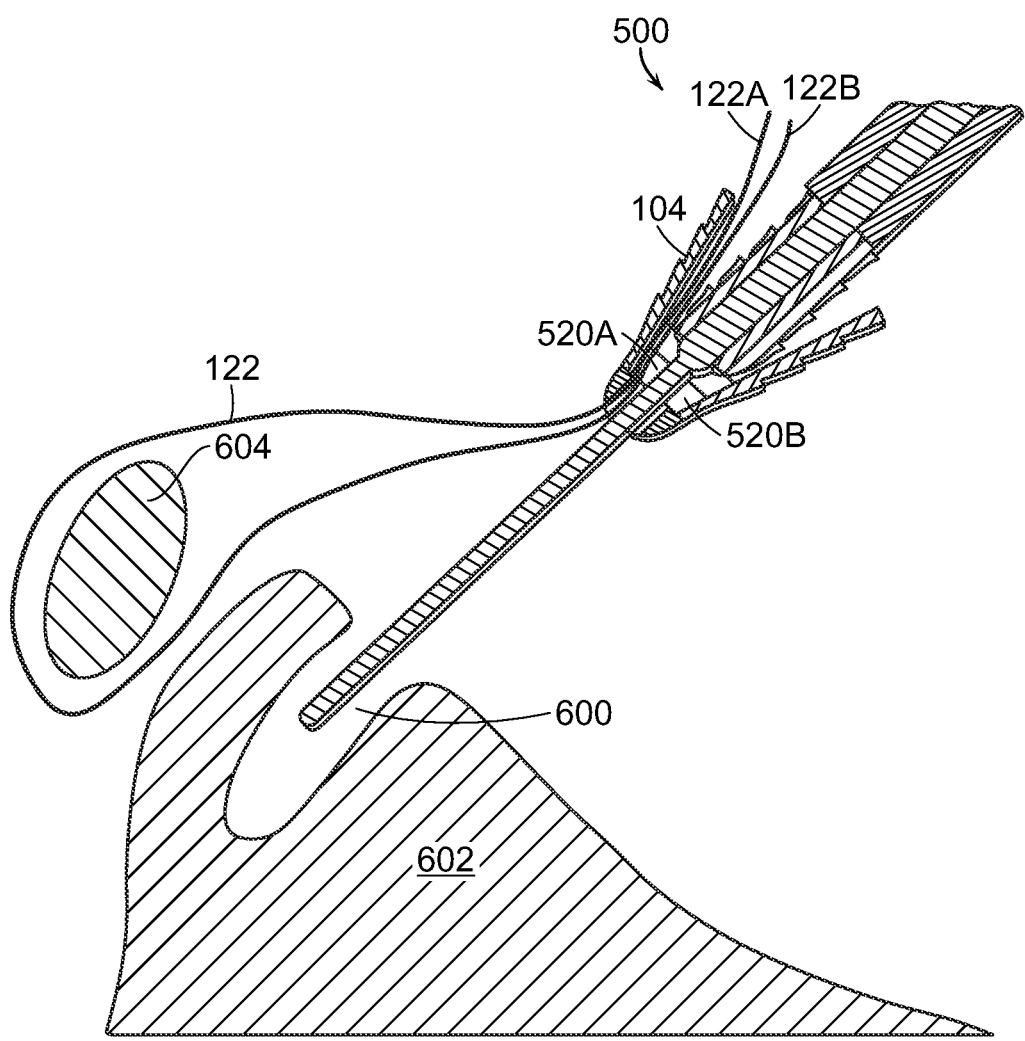
Figure 6C:
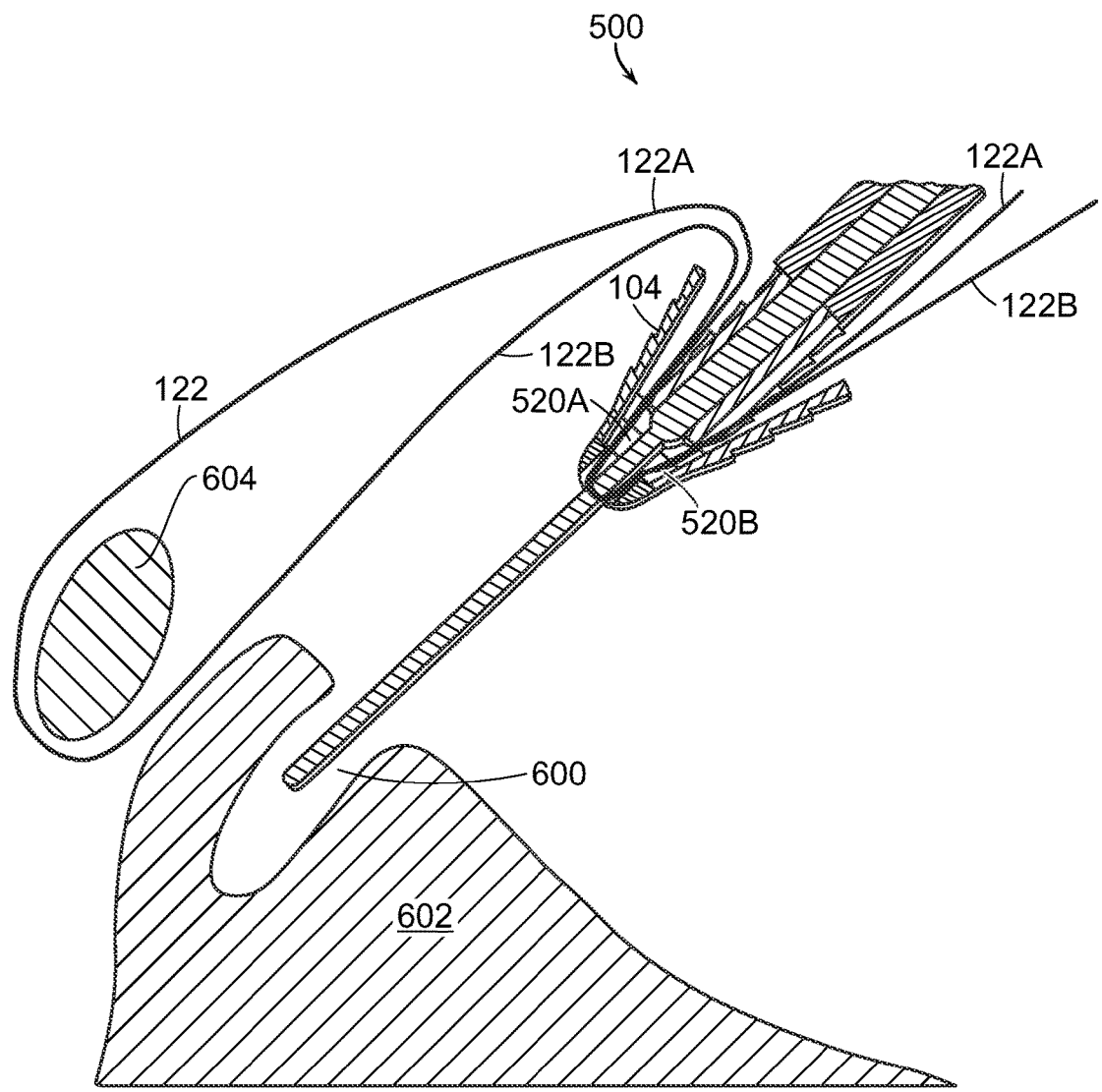

So configured, the suture anchor 100 is ready for disposal along the shaft 504 and into a recess, such as a drilled bone 602 (see, e.g., recess 600 of FIGS. 6A-6C). The recess 600 will generally possess a diameter smaller than the wings 104 such that insertion of the anchor 100 into the recess 602 draws the wings 104 into frictional engagement with the suture 122 by compression of the wings 104 against the recess.

An alternative embodiment of a suture anchor is illustrated in FIG. 5C. In this embodiment, the suture anchor 100 is segmented, as discussed above with respect to FIGS. 5A, 5B. The anchor 100 includes grooves 106 that extend along the length of the proximal anchor portion 510 and are dimensioned to mate with the wings 104, as discussed above.

FIGS. 6A-6C illustrate embodiments of suture routing through the anchor 100 in use with the inserter tool 500. In the embodiment of FIG. 6A, each end of the suture 122 (e.g., 122A, 122B) is routed through a different end of the transverse bore 110 (e.g., 520A, 520B). This routing may be accomplished by using a tool having two opposed wire loops and inserting each end the suture 122 through opposing wire loops prior to retraction of the wire loops from the anchor. As a result, when the wire loops are retracted from the anchor, the ends of the suture 122A, 122B will be drawn through opposing ends of the transverse bore 110 (e.g., 520A, 520B).

In the embodiment of FIG. 6B, both ends of the suture 122 are routed through a single end 520 of the transverse bore 110. This routing may be accomplished by using a tool having at least one wire loop and inserting each end of the suture 122 through a single wire loop prior to retraction of the one or more wire loops from the anchor 100. As a result, when the one or more wire loops are retracted from the anchor, each end of the suture 122 will be drawn through the same end 520 of the transverse bore 110.

In the embodiment of FIG. 6C, both ends of the suture 122 (e.g., 122A, 122B) enter the anchor body through a first end 520A of the transverse bore 110 and exit a second end 520B. This routing may be accomplished by using a tool having two opposed wire loops and inserting the suture ends 122A, 122B through each of the opposing wire loops 514 prior to retraction of the wire loops from the anchor. In such a suture loading, each of the suture ends 122A, 122B extend out from a single wire loop. As a result, when the wire loops are retracted from the anchor 100, the ends of the suture 122A, 122B will be drawn through a single ends of the transverse bore 110 (e.g., end 520B).

The terms comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method of inserting a suture anchor in a structure, comprising:
   inserting one or more wire loops through a longitudinal bore at a proximal end of a proximal anchor body of a suture anchor, the suture anchor comprising an elongate body, the elongate body further formed in two pieces including a distal anchor body and the proximal anchor body separate from one another and the longitudinal bore extending through each of the proximal and distal anchor bodies, such that the assembled elongate anchor body is cannulated;
   the proximal anchor body including a transverse bore located in a distal region of the proximal anchor body and extending through a width of the proximal anchor body, wherein the transverse bore extends through the proximal anchor body;
   the distal anchor body including one or more wings extending from an outer surface thereof, the one or more wings being positioned adjacent to the transverse bore of the proximal anchor body in an assembled configuration;
   advancing the one or more wire loops through the longitudinal bore until at least a portion of the one or more wire loops exits a distal end of the distal anchor body;
   inserting a suture through at least one of the one or more wire loops;

retracting the one or more wire loops through the longitudinal bore of the distal anchor body and at least one end of the transverse bore of the proximal anchor body, wherein first and second ends of the suture exit the anchor body through the at least one end of the transverse bore; and advancing the suture anchor into a recess, the recess having a diameter smaller than a diameter of the one or more wings, wherein the recess urges the one or more wings into frictional engagement with the suture by compression of the one or more wings against the recess.

2. The method of claim 1, wherein inserting the suture through at least one of the one or more wire loops comprises inserting the first end of the suture through a first wire loop and inserting the second end of the suture through a second wire loop and wherein, after retracting the one or more wire loops, the first end of the suture exits the anchor body through a first end of the transverse bore and the second end of the suture exits the anchor body through a second end of the transverse bore.

3. The method of claim 1, wherein inserting the suture through at least one of the one or more wire loops comprises inserting the first and second ends of the suture through a single wire loop and wherein, after retracting the one or more wire loops, the first and second ends of the suture exit the anchor body through a single end of the transverse bore.

4. The method of claim 1, wherein inserting the suture through at least one of the one or more wire loops comprises inserting the first and second ends of the suture through a first and a second wire loop and wherein, after retracting the one or more wire loops, the first and second ends of the suture enter the anchor body through a first end of the transverse bore and exit the anchor body through a second end of the transverse bore.

* * * * *